(12) United States Patent
Liu et al.

(10) Patent No.: US 7,351,770 B2
(45) Date of Patent: *Apr. 1, 2008

(54) IONIC HYDROPHILIC HIGH MOLECULAR WEIGHT REDOX POLYMERS FOR USE IN ENZYMATIC ELECTROCHEMICAL-BASED SENSORS

(75) Inventors: Zuifang Liu, Milton of Leys (GB); James Iain Rodgers, Lochardil (GB); Geoffrey Lillie, Inverness (GB); Marco Fabio Cardosi, Croy (GB)

(73) Assignee: Lifescan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/957,441

(22) Filed: Sep. 30, 2004

(65) Prior Publication Data

US 2006/0069211 A1    Mar. 30, 2006

(51) Int. Cl.
*C08F 271/02* (2006.01)

(52) U.S. Cl. ............... 525/283; 525/279; 525/297; 525/298; 435/4

(58) Field of Classification Search ........... 526/241; 525/279, 283, 297, 298; 435/4
See application file for complete search history.

(56) References Cited

U.S. PATENT DOCUMENTS

| | | | | |
|---|---|---|---|---|
| 3,238,185 A * | 3/1966 | Neuse | .................. | 526/221 |
| 3,322,793 A * | 5/1967 | Bozak | .................. | 549/209 |
| 3,326,948 A * | 6/1967 | Cais et al. | .............. | 556/31 |
| 3,350,369 A * | 10/1967 | Rosenberg et al. | ........ | 526/238 |
| 3,718,633 A * | 2/1973 | Baldwin et al. | .......... | 526/204 |
| 3,770,787 A * | 11/1973 | Burnett et al. | ........... | 556/144 |
| 3,813,307 A * | 5/1974 | Burnett et al. | ......... | 149/19.91 |
| 3,816,380 A * | 6/1974 | Reed, Jr. | ................. | 526/515 |
| 3,843,700 A * | 10/1974 | Stevens et al. | .......... | 556/145 |
| 3,847,871 A * | 11/1974 | Stephens et al. | ........ | 526/204 |
| 3,847,882 A * | 11/1974 | Baldwin et al. | .......... | 526/241 |
| 3,857,870 A * | 12/1974 | Stevens et al. | ........... | 556/145 |
| 3,886,190 A * | 5/1975 | Reed, Jr. | ................. | 556/144 |
| 3,886,191 A * | 5/1975 | Reed, Jr. | ................. | 556/144 |
| 3,886,192 A * | 5/1975 | Reed, Jr. | ................. | 556/144 |
| 4,224,125 A | 9/1980 | Nakamura et al. | | |
| 5,089,112 A | 2/1992 | Skotheim et al. | | |
| 5,225,064 A * | 7/1993 | Henkens et al. | ........ | 204/403.1 |
| 5,262,035 A | 11/1993 | Gregg et al. | | |
| 5,264,104 A * | 11/1993 | Gregg et al. | .......... | 204/403.09 |
| 5,264,105 A * | 11/1993 | Gregg et al. | .......... | 204/403.09 |
| 5,334,296 A * | 8/1994 | Henkens et al. | ........ | 205/777.5 |
| 6,284,478 B1 | 9/2001 | Heller et al. | | |
| 6,376,596 B1 * | 4/2002 | Barsotti et al. | ........... | 524/500 |
| 6,376,597 B1 * | 4/2002 | Coca et al. | ............... | 524/504 |
| 7,109,271 B2 * | 9/2006 | Liu et al. | .................. | 525/283 |
| 2003/0152823 A1 * | 8/2003 | Heller | ..................... | 429/43 |
| 2004/0099529 A1 * | 5/2004 | Mao et al. | ............ | 204/403.14 |
| 2004/0170596 A1 * | 9/2004 | Hauschel et al. | ....... | 424/78.19 |

FOREIGN PATENT DOCUMENTS

| | | | |
|---|---|---|---|
| WO | WO 03/025257 A1 | | 3/2003 |
| WO | WO 03025257 | * | 3/2003 |
| WO | WO 03025257 A1 | * | 3/2003 |

OTHER PUBLICATIONS

Hale, Paul D., et al., "Amperometric Glucose Biosensors based on Redox Polymer-Mediated Electron Transfer", Anal. Chem. 1991, 63, pp. 677-682.
Heller, Adam, Electrical Wiring of Redox Enzymes, Acc. Chem. Res. vol. 23, No. 5 1990, pp. 128-134.
Kuramoto, Noriyuki, et al., Property of thermo-sensitive and redox-active poly(N-cyclopropylacrylamide-co-vinylferrocene) and poly(N-Isopropylacrylamide-co-vinylferrocene), Polymer, vol. 39 No. 3, pp. 669-673, 1998.
Saito, Takahiro, et al., "Characterization of poly(vinylferrocene-co-2-hydroxyethyl methacrylate) for use as electron mediator in enzymatic glucose sensor", Reactive & Functional Polymers 37 (1998) pp. 263-269.
Extended European Search Report, European Patent Office dated Dec. 15, 2005, EP 05256103.2.

* cited by examiner

*Primary Examiner*—Randy Gulakowski
*Assistant Examiner*—M. Bernshteyn

(57) ABSTRACT

Ionic hydrophilic high molecular weight redox polymers for use in enzymatic electrochemical-based sensors include a hydrophilic polymer (such as a hydrophilic polymer backbone) with ionic portions (e.g., cationic monomers incorporated in the hydrophilic polymer backbone) and a plurality of attached redox mediators. The redox mediators can be, for example, covalently attached to the hydrophilic polymer in a pendant manner. An exemplary cationic hydrophilic high molecular weight redox polymer is synthesized by copolymerization of a hydrophilic acrylamide monomer, [2-(acryloyloxy)ethyl]trimethyl ammonium chloride and vinyl ferrocene.

13 Claims, 3 Drawing Sheets

IONIC HYDROPHILIC HIGH MOLECULAR WEIGHT REDOX POLYMERS FOR USE IN ENZYMATIC ELECTROCHEMICAL-BASED SENSORS

BACKGROUND OF THE INVENTION

1. Field of the Invention

The present invention relates, in general, to sensors and, in particular, to enzymatic electrochemical-based sensors.

2. Description of the Related Art

The use of enzymatic electrochemical-based sensors that employ a redox mediator (e.g., ferrocene) and a redox enzyme (such as glucose oxidase) in conjunction with an electrode(s) for the determination of an analyte in a liquid sample has become of heightened interest in recent years. Such enzymatic electrochemical-based sensors are believed to be particularly suitable for continuous or semi-continuous monitoring of analytes (for example, glucose) in bodily fluid samples (e.g., blood or interstitial fluid samples). For example, enzymatic electrochemical-based glucose sensors employing a redox mediator, a redox enzyme and a working electrode can determine (i.e., measure) glucose concentration using relatively low potentials (e.g., less than 0.4 V vs SCE), thereby limiting any interfering responses, at the working electrode. For a further description of enzymatic electrochemical-based sensors, see, for example, U.S. Pat. Nos. 5,089,112 and 6,284,478, each of which is hereby fully incorporated by reference.

Proteins surrounding a redox enzyme's redox center can preclude direct transfer of electrons from a redox enzyme to an electrode of an enzymatic electrochemical-based sensor. Therefore, in typical enzymatic electrochemical-based sensors, a redox mediator is employed to facilitate electron transfer between the redox enzyme(s) and an electrode(s) of the electrochemical-based sensor. In such a circumstance, the redox enzyme cycles between oxidized and reduced states, driven by the presence of analyte, the redox mediator and a surface of the electrode. The net result of such cycling is that electrons are either accepted or donated at the surface of the electrode while the redox enzyme essentially maintains its original oxidation state and catalytic characteristics.

For enzymatic electrochemical-based sensors that require long term stability, such as continuous or semi-continuous electrochemical-based glucose sensors, it is essential that both the redox mediator and the redox enzyme do not leach away from the vicinity of the electrode. Therefore, it is not desirable to employ readily leachable redox mediators (such as readily leachable ferricyanide, benzoquinone and low molecular weight quinone derivatives, ferrocene, low molecular weight ferrocene derivatives, ruthenium complexes and osmium complexes) in enzymatic electrochemical-based sensors. In addition, if the redox mediator is a substance that is harmful to humans or other subjects, leaching of the redox mediator into a human's or other subject's body is undesirable and thus to be avoided.

Furthermore, the redox enzyme and redox mediator of enzymatic electrochemical-based sensors must be able to favorably interact with one another and the redox mediator must be able to exchange electrons with an electrode of the enzymatic electrochemical-based sensor. In other words, the activity of both the redox enzyme and redox mediator should be maintained while inadvertent leaching is prevented.

To prevent redox mediator leaching, certain chemical compositions wherein redox mediators are chemically attached to redox enzymes have been proposed for use in electrochemical-based sensors. The redox enzymes of such chemical compositions can, however, suffer from a deleterious decrease in enzyme activity.

Alternatively, redox mediators have also been attached to water-insoluble synthetic polymer chains, such as polysiloxanes, in order to prevent leaching. However, such chemical compositions suffer from low flexibility, and thus a reduced mediation activity, due to their hydrophobic nature. In addition, the attachment of redox mediators to water insoluble synthetic polymer chains does not directly address the need to prevent leaching of the redox enzymes employed in enzymatic electrochemical-based sensors.

Still needed in the field, therefore, is a chemical composition for use in enzymatic electrochemical-based sensors that prevents inadvertent leaching of both redox mediators and redox enzymes from the vicinity of the electrochemical-based sensor's electrode while maintaining adequate activity of the redox mediator and redox enzyme.

SUMMARY OF THE INVENTION

Ionic hydrophilic high molecular weight redox polymers according to embodiments of the present invention prevent inadvertent leaching of both redox mediators and redox enzymes from the vicinity of an electrochemical-based sensor's electrode while maintaining adequate activity of the redox mediator and redox enzyme.

Ionic hydrophilic high molecular weight redox polymers for use in enzymatic electrochemical-based sensors according to embodiments of the present invention include a hydrophilic polymer with ionic portions (e.g., ionic monomers incorporated into the hydrophilic polymer backbone) and a plurality of attached redox mediators. The redox mediators can be, for example, covalently attached to the hydrophilic polymer in a pendant manner.

The molecular weight of the ionic hydrophilic redox polymer is sufficiently high that the redox polymer has a strong affinity towards, is readily immobilized on, is readily incorporated in, and/or readily entrapped in the vicinity of an electrode (e.g., a carbon-based working electrode) of an enzymatic electrochemical-based sensor. Therefore, the typical molecular weight of ionic hydrophilic redox polymers according to the present invention is greater than 16 Kg/mol.

The ionic nature of ionic hydrophilic high molecular weight redox polymers according to embodiments of the present invention fosters a strong association with charged redox enzymes (such as glucose oxidase). This strong association both minimizes leaching of the redox enzyme and fosters activity between the redox enzyme and the redox mediator.

Ionic hydrophilic high molecular weight redox polymers according to embodiments of the present invention can be synthesized by, for example, free radical co-polymerization of a mediator-containing monomer (such as vinyl ferrocene (VFc)), a hydrophilic monomer and an ionic monomer. In such a synthesis, the hydrophilic monomer can be employed to synthesize a major portion of a hydrophilic polymeric backbone within the redox polymer. The hydrophilic nature of the resulting ionic hydrophilic high molecular weight redox polymer provides for swelling and/or solubility of the ionic hydrophilic high molecular weight redox polymer in an aqueous solution (such as an aqueous bodily fluid).

The use of an ionic monomer results in the incorporation of an ionic portion (i.e., a charged functionality) in the ionic hydrophilic high molecular weight redox polymer, while the use of a mediator-containing monomer results in a mediator being attached to the ionic hydrophilic high molecular weight redox polymer.

BRIEF DESCRIPTION OF DRAWINGS

A better understanding of the features and advantages of the present invention will be obtained by reference to the following detailed description that sets forth illustrative embodiments, in which principles of the invention are utilized, and the accompanying drawings of which.

DETAILED DESCRIPTION OF THE INVENTION

To be consistent throughout the present specification and for clear understanding of the present invention, the following definitions are hereby provided for terms used therein:

The term "redox mediator" refers to any chemical moiety capable of undergoing a reduction (accepting of an electron(s)) or oxidation (donation of an electron(s)) with both an electrode surface and a redox enzyme.

The term "redox enzyme" refers to biochemical capable of specifically catalyzing the oxidation or reduction of a substrate molecule.

The term "hydrophilic" refers to any chemical species or subgroup with a high affinity for water or aqueous solutions. Therefore, a hydrophilic compound will tend to be attracted to, dissolve in, or be absorbed in water or an aqueous solution.

The term "redox polymer" refers to a polymer that has been synthesized or modified (e.g., derivatized) to include at least one redox mediator.

Figure 1:
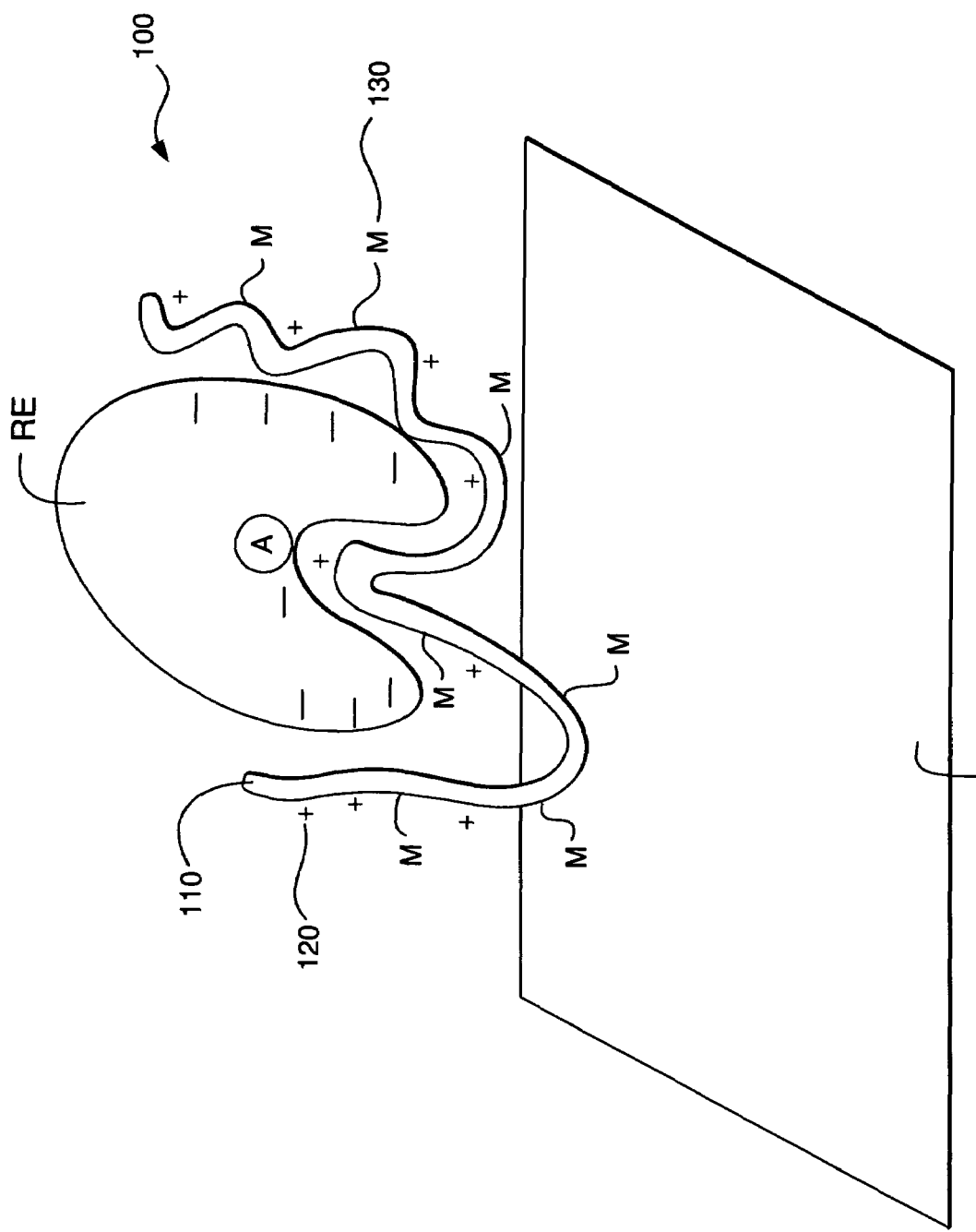
FIG. 1 is a simplified schematic representation of an exemplary embodiment of an ionic hydrophilic high molecular weight redox polymer according to the present invention in the vicinity of a redox enzyme and an electrode of an enzymatic electrochemical-based sensor.

FIG. 1 is a simplified schematic depiction of a cationic hydrophilic high molecular weight redox polymer 100 for use in enzymatic electrochemical-based sensors. FIG. 1 depicts cationic hydrophilic high molecular weight redox polymer 100 in the vicinity of an electrode (E) of an enzymatic electrochemical-based sensor and a negatively charged redox enzyme (RE). The negative charge of redox enzyme RE is depicted by "−" symbols in FIG. 1 while a redox center of redox enzyme RE is depicted by a capital "A."

Cationic hydrophilic high molecular weight redox polymer 100 includes a hydrophilic polymer backbone 110 with ionic portions 120 (depicted by the "+" symbols in FIG. 1) and a plurality of attached redox mediators 130 (depicted by the "M" symbol in FIG. 1). Once apprised of the present disclosure, one skilled in the art will recognize that although cationic hydrophilic high molecular weight redox polymer 100 and hydrophilic polymer backbone 110 are both hydrophilic when considered as a whole, ionic portions 120 and redox mediators 130 need not necessarily be hydrophilic.

The molecular weight of cationic hydrophilic high molecular weight redox polymer 100 is typically greater than 16 Kg/mol. In this regard, it should be noted that a relatively high molecular weight does not necessarily lead to a permanently high affinity between a cationic hydrophilic high molecular weight redox polymer and an electrode. However, for the circumstance where the cationic hydrophilic high molecular weight redox polymer is not entrapped in the vicinity of an electrode, high molecular weights are associated with relatively slow dissolution rates and beneficially slow leaching.

Hydrophilic polymer backbone 110 can be formed from any suitable hydrophilic polymer(s) known to those skilled in the art. For example, hydrophilic polymer backbone 110 can be formed from a hydrophilic acrylamide monomer (AAM). Alternative hydrophilic monomers suitable for use in embodiments of the present invention include, but are not limited to, hydrophilic monomers with a polymerizable acrylate or vinyl group, such as hydroxyethyl methacrylate, glycerol methacrylate, N-vinylpyrrolidinone and N-isopropylacrylamide.

Ionic portions 120 can be any suitable ionic portions known to those of skill in the art including, for example, cationic units (e.g., monomers) incorporated to hydrophilic polymer backbone 110. Suitable cationic monomers include, but are not limited to, [2-(acryloyloxy)ethyl]trimethyl ammonium chloride (AETMAC). Alternative cationic monomers suitable for use in the present invention include quaternary ammonium cationic monomers and tertiary ammonium cationic monomers, such as (3-acrylamidopropyl) trimethyl ammonium chloride, [3-(methacryloylamino)propyl]trimethyl ammonium chloride, [(2-methacryloyloxy)ethyl]trimethyl ammonium chloride, vinylbenzyl trimethyl ammonium chloride, 2-(dimethylamino)ethyl methacrylate and 2-(diethylamino)ethyl methacrylate.

If desired, embodiments of anionic hydrophilic high molecular weight redox polymers according to the present invention can be formed via incorporation of suitable anionic portions into a hydrophilic polymer backbone. Suitable anionic portions include, for example, carboxylic acid monomers (e.g., acrylic acid, methacrylic acid, and maleic and hydride monomers). An anionic hydrophilic high molecular weight redox polymer can be beneficially employed with a cationic redox enzyme. For example, glucose dehydrogenase (GDH) is weakly cationic at a pH of 7.

Redox mediators 130 can be, for example, covalently attached to hydrophilic polymer backbone 110 in a pendant manner. Redox mediator 130 can be any suitable redox mediator known to one skilled in the art including, but not limited to ferrocene (Fc), osmium complexes, quinones, ferricyanide, methylene blue, 2,6-dichloroindophenol, thionine, gallocyanine and indophenol.

For determining an analyte (e.g. glucose) in an aqueous solution (e.g. blood and ISF), the hydrophilic nature of cationic hydrophilic high molecular weight redox polymer 100 facilitates a favorable interaction between redox mediator 130 and redox enzyme RE for electron exchange, as well as a favorable interaction between redox mediator 130 and electrode E for electron exchange. In addition, the cationic nature of cationic hydrophilic high molecular weight redox polymer 100 enhances interaction with negatively charged (i.e., anionic) redox enzyme RE.

The relatively high molecular weight of ionic hydrophilic high molecular weight redox polymers according to embodiments of the present invention facilitates their use with enzymatic electrochemical-based sensors in a manner that prevents inadvertent leaching of the redox mediator and/or redox enzyme. For example, the high molecular weight can facilitate an affinity with an electrode of the enzymatic electrochemical-based sensor.

Figure 2:
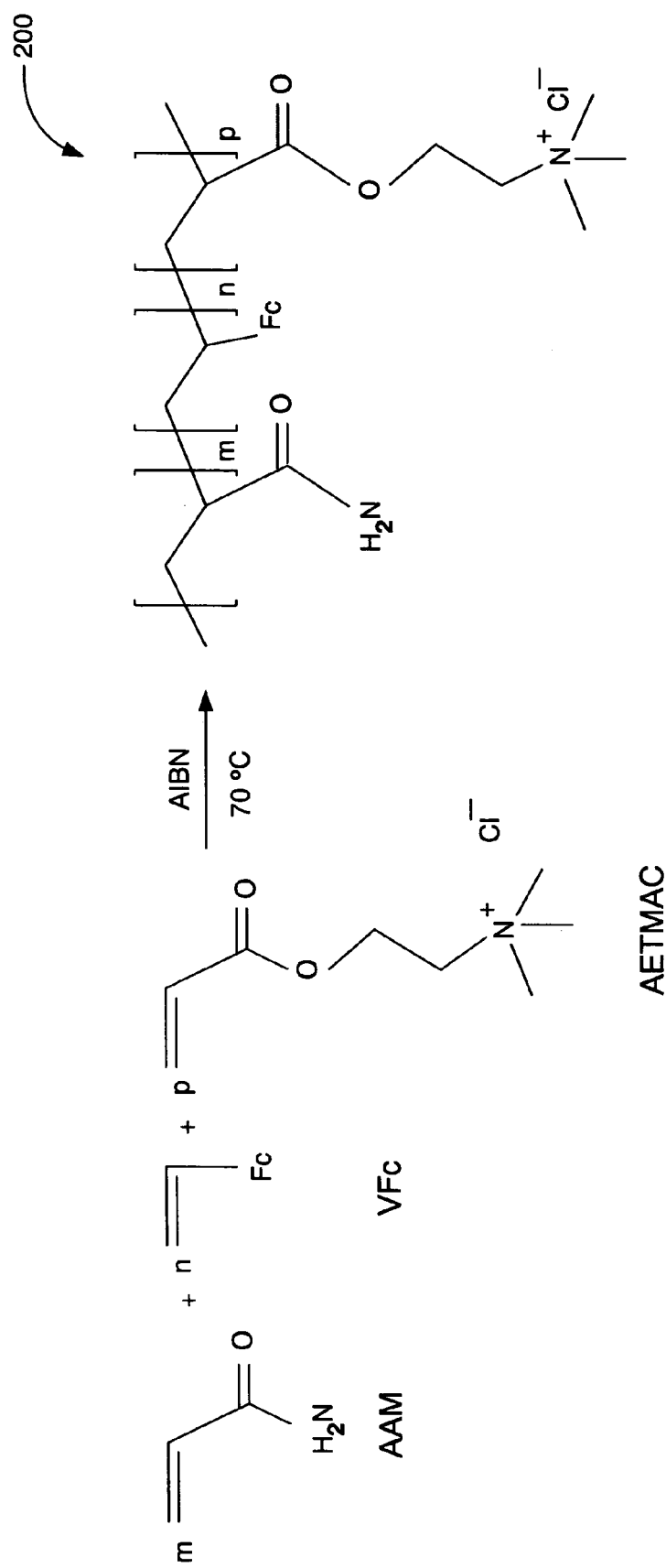
FIG. 2 is a simplified representation of a reaction sequence for synthesizing an ionic hydrophilic high molecular weight redox polymer according to an exemplary embodiment of the present invention.

FIG. 2 is a simplified representation of a simple one-step reaction sequence for synthesizing an ionic hydrophilic high molecular weight redox polymer 200 according to an exemplary embodiment of the present invention. The reaction sequence involves the co-polymerization of acrylamide (AAM), vinyl ferrocene (VFc), and [2-(acryloyloxy)ethyl] trimethyl ammonium chloride (AETMAC), as shown in FIG. 2. The reaction sequence of FIG. 2 is conducted at 70° C. using 2,2'-azobisisobutyronitrile (AIBN) as an initiator.

The ionic hydrophilic high molecular weight redox polymer 200 that results from the reaction sequence of FIG. 2 can have, for example, a high molecular weight of approximately 110 Kg/mol (measured as a weight average molecular weight by gel permeation chromatography (GPC)).

It should be noted that AAM is employed in the reaction sequence of FIG. 2 because AAM has a relatively high chain propagation rate coefficient that assists in the formation of a relatively high molecular weight redox polymer.

In FIG. 2, the relative molar portions of AAM, VFc, and AETMAC are represented as m, n and p, respectively. In this regard, m can, for example, be in the range of from about 84 to about 99, n can be, for example, in the range from about 1 to about 6, and p can be, for example, in the range of from nearly 0 to about 10.

The physical conformation of ionic hydrophilic high molecular weight redox polymer 200 is highly flexible such that portions thereof can segmentally diffuse between a redox enzyme's redox center and an electrode of an enzymatic electrochemical-based sensor to realize rapid electron exchange. In this regard, the term "segmentally diffuse" refers to portions (e.g., redox mediator containing portions) that can become solvated and move about while remaining attached (tethered) to the ionic high molecular weight redox polymer.

The cationic portion of ionic hydrophilic high molecular weight redox polymer 200 fosters an affinity with negatively charged redox enzymes (such as, for example, glucose oxidase). In this regard, affinity between ionic hydrophilic high molecular weight redox polymer 200 and glucose oxidase has been observed in the form of flocculation when they were combined in an aqueous solution. Such an affinity enables rapid electron exchange between the redox mediator and the redox enzyme since the ionic charge provides for a close contact with the redox enzyme's redox center (also known as the redox enzyme's active center).

EXAMPLE 1

Synthesis of an Ionic Hydrophilic High Molecular Weight Redox Polymer

Ionic hydrophilic high molecular weight redox polymer 200 of FIG. 2 was synthesized by a free radical co-polymerization using a reaction solution of 1.8 g of acrylamide (AAM), 0.7 g of 80% [2-(acryloyloxy)ethyl]trimethyl ammonium chloride (AETMAC), 0.3 g of vinylferrocene (VFc), and 0.03 g of 2,2'-azobisisobutyronitrile (AIBN) in a 40 mL mixture of dioxane and ethanol (1/1 v/v). The reaction was performed in a round bottom flask.

Before initiating the reaction, the reaction solution was deoxygenated by bubbling nitrogen for one hour. The reaction solution was then heated to 70° C. in an oil bath for 24 hours with continuous magnetic agitation under a nitrogen atmosphere. The resulting polymer precipitates were filtered off and repeatedly washed with acetone to provide a purified sample of ionic hydrophilic high molecular weight redox polymer 200. The purified sample was subsequently dried in an oven at 50° C.

Relatively low molecular weight portions of the purified and dried sample were then eliminated through dialysis against de-ionized water. The dialysis employed a cellulose membrane dialysis tubing with a molecular cutoff of 16 Kg/mol.

EXAMPLE 2

Preparation of an Enzymatic Electrochemical-Based Glucose Sensor Electrode Employing an Ionic Hydrophilic High Molecular Weight Redox Polymer An enzymatic electrochemical-based glucose sensor electrode was prepared by applying 0.5 μL of a 1% (w/v) aqueous solution of ionic hydrophilic high molecular weight redox polymer 200 (prepared as in Example 1 above) onto a carbon electrode (2.25 mm×2.25 mm in size) followed by drying in an oven at 50° C. for about 5 minutes to form a redox polymer coated electrode. Next, 1 μL of a 10% (w/v) glucose oxidase solution in phosphate buffered saline (PBS) was applied to the redox polymer coated electrode and then dried in the oven at 50° C. for 10 minutes.

A solution containing 52 mg of polyethylenimine (PEI) and 106 mg of poly(propylene glycol) diglycidyl ether (PPGDGE) was mixed in 1 mL 2-isopropanol. Next, 0.8 μL of the PEI/PPGDGE mixture was applied to the electrode prepared as described immediately above and dried in the oven at 50° C. for 30 minutes. The PEI and PPGDGE formed a cross-linked dialysis membrane which retained ionic hydrophilic high molecular weight redox polymer 200 and the glucose oxidase (a redox enzyme) in the vicinity of the electrode whilst allowing small molecular weight analytes, such as glucose, to penetrate therethrough.

EXAMPLE 3

Testing of the Enzymatic Electrochemical-Based Sensor Electrode of Example 2

The electrochemical glucose sensor electrode of Example 2 was tested as a working electrode in a three-electrode sensor system in PBS over a glucose concentration range from 0 mM to 15 mM. The three-electrode sensor system included a working electrode, counter electrode and reference electrode.

The working electrode was poised at 300 mV vs Ag/AgCl with the three-electrode sensor system open to the atmosphere at room temperature and under gentle magnetic agitation. Boluses of a concentrated glucose solution were periodically added to the PBS to increase the glucose concentration of the PBS. FIG. 3A shows that the current of the three-electrode sensor system increased rapidly and then reached plateaus following the addition of each bolus.

The working electrode was also tested continuously for ten hours at 15 mM of glucose (not shown in FIG. 3A) and exhibited a current response decline of only about 17%. Such a response is a dramatic improvement in long-term measurement stability compared with enzymatic electrochemical-based sensors employing small molecular redox mediators.

Figure 3B:
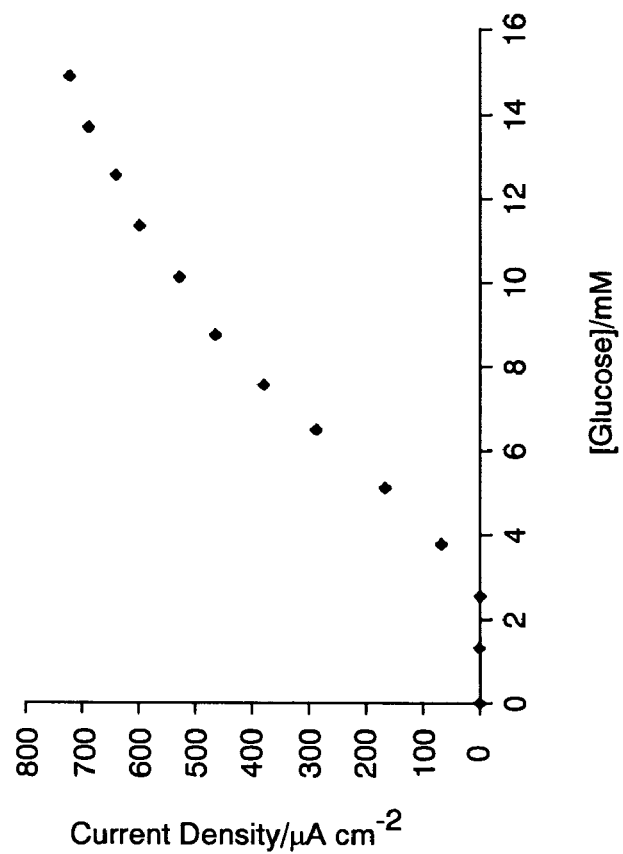
FIG. 3B is a calibration curve corresponding to the transient current response of FIG. 3A.
Figure 3A:
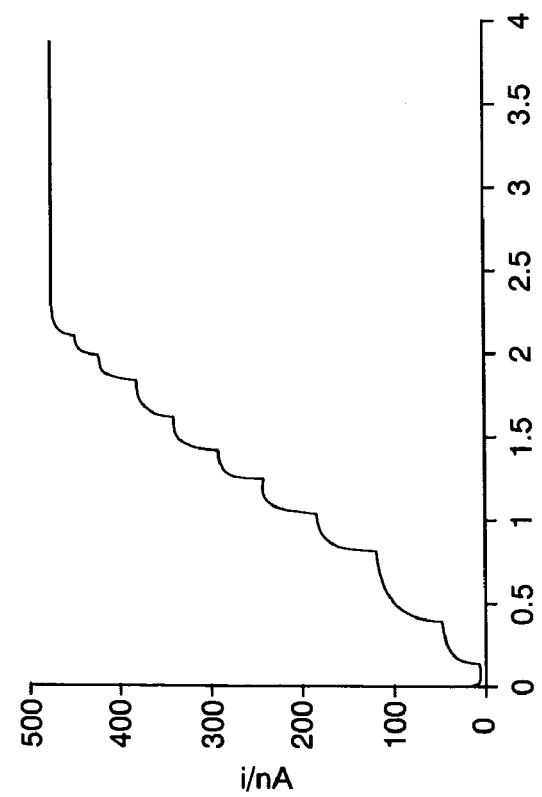
FIG. 3A represents a transient current response of an enzymatic electrochemical-based glucose sensor that included a cationic hydrophilic high molecular weight redox polymer according to an exemplary embodiment of the present invention tested with sequentially spiked boluses of glucose.

FIG. 3B is a calibration curve corresponding to FIG. 3A depicting current response versus glucose concentration. This calibration curve is approximately linear in the range between 2 mM and 15 mM.

Ionic hydrophilic high molecular weight redox polymers according to embodiments of the present invention can be easily synthesized. In addition, the molecular weight, ionic properties and physical conformation can be adapted to provide for a high electrode affinity and redox activity (for example, fast electron transfer with redox enzymes).

It should be understood that various alternatives to the embodiments of the invention described herein may be employed in practicing the invention. It is intended that the following claims define the scope of the invention and that structures within the scope of these claims and their equivalents be covered thereby.

What is claimed is:

1. An ionic hydrophilic high molecular weight redox polymer for use in enzymatic electrochemical-based sensors employing a charged redox enzyme, the ionic hydrophilic high molecular weight redox polymer comprising:
   a hydrophilic polymer backbone that includes ionic portions; and
   a plurality of attached redox mediators covalently attached to the hydrophilic polymer backbone in a flexible pendant manner such that the redox mediators can segmentally diffuse between the charged redox enzyme and an electrode of the enzymatic electrochemical-based sensor,
   wherein the molecular weight of the ionic hydrophilic high molecular weight polymer is greater than 16 Kg/mol as a weight average molecular weight, and
   wherein an ionic charge of the ionic portions is predetermined to result in an affinity between the ionic portions and the charged redox enzyme of an enzymatic electrochemical-based sensor and that minimizes leaching of the redox enzyme and fosters activity between the redox enzyme and redox mediator.

2. The ionic hydrophilic high molecular weight redox polymer of claim 1, wherein the hydrophilic polymer backbone is formed at least partially from a hydrophilic acrylamide monomer (AAM).

3. The ionic hydrophilic high molecular weight redox polymer of claim 1, wherein the hydrophilic polymer backbone is formed at least partially from at least one of hydrophilic monomers with an acrylate polymerizable group and hydrophilic monomers with a vinyl polymerizable group.

4. The ionic hydrophilic high molecular weight redox polymer of claim 1, wherein the ionic portions are cationic portions.

5. The ionic hydrophilic high molecular weight redox polymer of claim 1, wherein the ionic portion is formed of [2-(acryloyloxy)ethyl]trimethyl ammonium chloride (AETMAC).

6. The ionic hydrophilic high molecular weight redox polymer of claim 1, wherein the ionic portion is formed of at least one of a quaternary ammonium cationic monomer and a tertiary ammonium cationic monomer.

7. The ionic hydrophilic high molecular weight redox polymer of claim 1, wherein the redox mediator is ferrocene (Fc).

8. The ionic hydrophilic high molecular weight redox polymer of claim 1, wherein:
   the hydrophilic polymer is a hydrophilic polymer backbone formed at least partially from hydrophilic acrylamide monomer (AAM);
   the ionic portion is formed at least partially from [2-(acryloyloxy)ethyl]trimethyl ammonium chloride (AETMAC) incorporated in the hydrophilic polymer backbone; and
   the redox mediator is ferrocene (Fc) covalently attached to the hydrophilic polymer backbone in the form of vinyl ferrocene (VFc).

9. The ionic hydrophilic high molecular weight redox polymer of claim 8, wherein the molecular weight is approximately 110 Kg/mol as a weight average molecular weight.

10. The ionic hydrophilic high molecular weight redox polymer of claim 8, wherein the relative molar portion of AAM is in the range of about 84 to about 99, the relative molar portion of VFc is in the range of about 1 to about 6 and the relative molar portion of AETMAC is in the range of from nearly zero to about 10.

11. The ionic hydrophilic high molecular weight redox polymer of claim 1, wherein the ionic portion is formed of a carboxylic acid monomer.

12. The ionic hydrophilic high molecular weight redox polymer of claim 1, wherein the ionic hydrophilic high molecular weight redox polymer is a cationic hydrophilic high molecular weight redox polymer.

13. The ionic hydrophilic high molecular weight redox polymer of claim 1, wherein the ionic hydrophilic high molecular weight redox polymer is an anionic hydrophilic high molecular weight redox polymer.

* * * * *